United States Patent [19]

Smalley et al.

[11] 4,060,460
[45] Nov. 29, 1977

[54] REMOVAL OF CHLOROPRENES FROM ETHYLENE DICHLORIDE

[75] Inventors: Edmund W. Smalley, Brewerton; Bruce Edward Kurtz, Marcellus; Bhaskar Bandyopadhyay, Camillus, all of N.Y.

[73] Assignee: Allied Chemical Corporation, Morris Township, N.J.

[21] Appl. No.: 580,077

[22] Filed: May 22, 1975

[51] Int. Cl.$^2$ ............................................. C07C 17/38
[52] U.S. Cl. .................................. 203/29; 260/652 P; 203/31
[58] Field of Search ..................... 260/652 P, 654 S; 203/29, 31, 71

[56] References Cited

U.S. PATENT DOCUMENTS 2,748,176  5/1976  Morris ............................. 260/652 P

FOREIGN PATENT DOCUMENTS 1,959,211  6/1970  Germany ......................... 260/652 P Primary Examiner—Delbert E. Gantz
Assistant Examiner—J. Thierstein
Attorney, Agent, or Firm—Gerhard H. Fuchs

[57] ABSTRACT

Process is provided for removal of chloroprenes as impurities from ethylene dichloride streams formed in the production of vinyl chloride by the thermal cracking of ethylene dichloride. The ethylene dichloride stream is subjected to distillation in a distillation zone to which free chlorine gas is introduced, thereby chlorinating the chloroprenes contained therein and forming higher boiling chlorocarbons as reaction products. The higher boiling chlorocarbons, together with ethylene dichloride, may be removed as bottoms and passed to a second distillation zone for separation of ethylene dichloride from the higher boiling impurities, thereby producing a substantially pure ethylene dichloride which may be recycled to the cracking step.

6 Claims, No Drawings

REMOVAL OF CHLOROPRENES FROM ETHYLENE DICHLORIDE

BACKGROUND OF THE INVENTION

1. Field of the Invention

This invention relates to a process for removing chloroprenes from an ethylene dichloride stream containing the same and more particularly to a process for removing the chloroprenes by chlorination to higher boiling chlorocarbons.

2. Description of the prior Art

The process of cracking ethylene dichloride (i.e., 1,2-dichloroethane) to form vinyl chloride and hydrogen chloride is a well known method of producing vinyl chloride monomer which finds wide use in industry in the preparation of polyvinyl chloride. Generally, only a portion of the ethylene dichloride fed to the cracking furnace is converted to vinyl chloride. The remainder, typically from about 30–70 weight percent of the ethylene dichloride feed, passes through the furnace unreacted and must be recycled for most efficient operation. The ethylene dichloride/vinyl chloride product stream exiting the cracking furnace, which generally contains from about 19 to 44 weight percent vinyl chloride and from 11 to 26 weight percent hydrogen chloride, is typically passed to a series of distillation columns, wherein hydrogen chloride and vinyl chloride are individually recovered in succeeding distillations. The crude ethylene dichloride stream which results as bottoms from the column in which vinyl chloride is collected at the head may then be recovered for recycle to the cracking furnace for production of additional vinyl chloride.

However, recovery of the unreacted ethylene dichloride from the crude ethylene dichloride stream is made more complicated by the presence of impurities which are produced in the cracking step. Of these impurities, the "chloroprenes", are one of the major undesired reaction by-products, and typically comprise up to 1 or more weight percent of the crude ethylene dichloride recycle stream. As used herein, the terms "chloroprenes" and "chloroprene impurities" are intended to include chloroprene (i.e. 2-chloro-1,3-butadiene) and alpha-chloroprene (i.e. 1-chloro-1,3-butadiene). Other impurities which the crude ethylene dichloride stream may contain include such compounds as 1,1-dichloroethane, ethyl chloride and benzene.

The presence of such impurities in an ethylene dichloride stream recycled to the cracking furnace is undesirable since some of these impurities, such as the chloroprenes, have been shown to increase the rate of coke formation in the coils of the cracking furnace, thereby requiring more frequent decoking of these coils, resulting in a loss of vinyl chloride monomer production due to equipment downtime. Thus, it is desired to purify the crude ethylene dichloride stream. Typically, such purification is undertaken by subjecting this ethylene dichloride stream to a series of distillations. In the first distillation, it is attempted to remove those impurities which boil at temperatures lower than that of ethylene dichloride (83.5° C. at 1 atm.) thereby resulting in a distilled bottoms containing the majority of the ethylene dichloride together with high boiling impurities. These bottoms may be passed to a second distillation zone wherein the ethylene dichloride is removed as distillate. While this purification scheme generally results in an ethylene dichloride feed substantially free of the undesired impurities, distillation in the first column, herein termed the "lights column", to remove the low boiling impurities results in a distillate which contains some ethylene dichloride (typically 30 to 60 weight percent ethylene dichloride) in addition to the undesired low boiling impurities such as the chloroprenes. Since in an industrial process discarding this distillate would result in a substantial loss of ethylene dichloride, it is necessary to recycle at least a portion of this distillate for more complete recovery of the ethylene dichloride content thereof. Thus, the bulk of the lights column condensate is typically returned as reflux to the lights column, a small purge stream being generally withdrawn to prevent buildup of the low boilers in the system.

However, such a scheme results in a purge stream from the lights column condensate which may contain up to about 30 weight percent of the chloroprenes, thereby presenting a serious waste disposal problem. Moreover, the chloroprenes present in the condensate can undergo spontaneous polymerization even at room temperature, forming high molecular weight, rubber-like polymers which are insoluble in the organic medium and which tend to foul the lights column and thereby increase the down-time for column cleaning. This spontaneous chloroprenes polymerization is catalyzed by the decomposition of polymeric peroxides which are formed upon reaction of chloroprene with air above temperatures of about 0° C. Thus, it is highly desirable to remove this potential source of column fouling and waste disposal problems.

While processes such as those disclosed in Great Britain Pat. No. 1,323,038 (1973) and U.S. Pat. No. 3,696,015 (P. Wirtz et al. 1972) have been developed for the removal of chloroprenes either prior to or after removal of low boiling impurities from the ethylene dichloride recycle stream, no process has been developed which would avoid the substantial costs due to increased equipment requirements which result from such prior art processes.

SUMMARY OF THE PRESENT INVENTION

In accordance with the present invention, an improved process for removing chloroprenes from an ethylene dichloride stream containing the same is provided which comprises passing the ethylene dichloride stream to a distillation zone, introducing free chlorine gas into the distillation zone and distilling the ethylene dichloride stream under conditions sufficient to chlorinate at least a portion of said chloroprenes. The distillate may be condensed and a portion of the condensate recycled as reflux to the distillation zone. A mixture containing ethylene dichloride in addition to the chlorination reaction products, as well as other impurities boiling at temperatures higher than ethylene dichloride, is recovered as distilled bottoms and may be passed to a second distillation zone wherein the ethylene dichloride is recovered as distillate, thereby removing said ethylene dichloride from the higher boiling impurities. The substantially pure ethylene dichloride thereby obtained may then be recycled to a cracking furnace for production of vinyl chloride monomer.

The process of the present invention has been found to result in efficient conversion of the chloroprenes content of the ethylene dichloride recycle feed stream to high boiling chlorocarbons (herein termed "chloroprene reaction products"), which are believed to comprise higher boiling trichlorobutenes, e.g. 1,2,4-trichloro-2-butene. These higher boiling impurities are recovered from the lights column together with the ethylene dichloride as distilled bottoms and may be efficiently separated therefrom in a subsequent distillation step. Thus, the present invention operates to substantially reduce the chloroprenes content of the distillates in the lights column, thereby resulting in a distillate condensate which is substantially free of said chloroprenes and which may be recycled to the distillation zone for more efficient recovery of the ethylene dichloride content thereof. Further, the process of the present invention substantially reduces the waste disposal problem associated with purged lights column condensate streams containing substantial quantities of chloroprenes. Moreover, it has been found that the distillate condensate so produced may be marketed as a source of chlorine as well as its ethylene content, and thus finds use in the preparation of industrial organic solvents.

DETAILED DESCRIPTION OF THE INVENTION

As mentioned above, the ethylene dichloride stream obtained from the cracking of ethylene dichloride in the production of vinyl chloride, is fed (after treatment for recovery of vinyl chloride and hydrogen chloride) to the lights column for removal therefrom of impurities which boil at a temperature lower than that of ethylene dichloride. As used herein, the term "crude ethylene dichloride stream" is intended to refer to the process stream containing ethylene dichloride and impurities which is obtained following treatment of the EDC stream exiting the cracking furnace for recovery of VCM and HCl therefrom. While the composition of the crude ethylene dichloride stream may vary widely, it typically contains from about 80 to 98 weight percent ethylene dichloride; and from about 0.05 to 6 weight percent chloroprenes. In addition, the ethylene dichloride stream may also contain from about 2 to 20 weight percent of other impurities, such as 1,1-dichloroethane, ethyl chloride, benzene and any residual vinyl chloride and hydrogen chloride not removed in previous recovery steps.

The mass flow rate of the ethylene dichloride stream which is passed to the distillation zone is not critical and may vary widely depending on the capacity of the distillation apparatus, the purity of the feed stream with respect to ethylene dichloride and other factors. The chlorine may be introduced to the distillation zone as a elemental chlorine-containing gas and may be introduced either batchwise, semi-continuously or continuously and at a wide variety of flow rates. However, the elemental chlorine-containing gas is generally introduced to the distillation zone at a mass flow rate which is not greater than 80 percent, preferably 56 to 72 percent, and most preferably 60 to 68 percent, of the mass flow rate of the chloroprenes fed to the distillation zone via the ethylene dichloride stream. While the chlorine-containing gas may be introduced to the distillation zone at a mass flow rate which exceeds 80 percent of the mass flow rate of chloroprenes fed to the distillation zone, this results in unreacted chlorine and tends to promote the substitution reaction of the chlorine and chloroprenes to form 1,4-chlorination products such as 1,4-dichloro-1,3-butadiene, in addition to hydrogen chloride. The production of hydrogen chloride is undesirable since its presence leads to corrosion in the equipment and also consumes additional chlorine which could otherwise be employed in the chlorination of the chloroprenes. Thus, it is desired to promote the addition reaction wherein higher boiling trichlorobutenes may be formed, while at the same time avoiding promotion of the substitution reaction, wherein hydrogen chloride is formed as by-product. The temperature of the chlorine-containing gas introduced to the distillation zone is not critical.

The chlorine-containing gas introduced to the distillation zone in accordance with the present invention may be obtained from a variety of sources, for example, by electrolytic decomposition of sodium chloride, and thus may also contain other gases such as hydrogen, oxygen and carbon dioxide in amounts up to about 10 volume percent. For most efficient operation, however, the chlorine gas preferably contains at least 95 volume percent chlorine. The chlorine gas preferably contains less than about 100 ppm, and most preferably less than 50 ppm, water vapor to avoid corrosion problems encountered due to adsorption by the water of residual HCl in the distillation zone.

For most efficient operation, it has been found that chlorine should be introduced to the distillation zone at a point where the quantity of liquid above the chlorine feed point is sufficient to allow substantially complete chlorination (i.e. chlorination of at least about 80 weight percent, and most preferably at least about 90 weight percent, of chloroprenes in the ethylene dichloride stream) of the chloroprenes contained in the feed stream. Where the distillation zone comprises a distillation column, chlorine should, therefore, be introduced to the column at a point where the liquid hold-up above the chlorine feed point is sufficient to allow substantially complete chlorination of the chloroprenes. The determination of the chlorine feed point in a given distillation column can be determined by conventional methods, and will of course vary depending upon the temperature of distillation. Thus, for example, under steady state conditions in a distillation column operating at an effective average temperature of from about 60° to 70° C., the minimum liquid hold-up above the chlorine feed point which would allow substantially complete chlorination of the maximum quantity of chloroprenes in the ethylene dichloride feed is given by the expression:

$$H_{min} \text{ (lbs)} = (C_{max} \text{ (lbs/hr)})/(r)$$

wherein $r = 0.523$ hour$^{-1}$ and is a rate constant calculated where the rate of chlorination of chloroprenes is just limited by the chlorine addition rate, and wherein $H_{min}$ is the minimum liquid hold-up in pounds and $C_{max}$ is the mass rate of flow of chloroprenes (i.e. chloroprene and alpha-chloroprene) introduced into the distillation zone with the ethylene dichloride stream.

Of course, the actual hold-up in the distillation zone between the chlorine feed point and the highest liquid level in the distillation zone may be calculated by standard methods. For example, where a distillation column is employed, the actual liquid hold-up ($H_{actual}$) between the selected chlorine feed point and the top of the column may be calculated as follows:

$$H_{actual} = (t)(A_t)(A_e)(h)(d)$$

wherein $t$ is the number of trays between the chlorine feed point and the top of the column, $A_t$ is the area of a tray, $A_e$ is the effective area of a tray, $h$ is the average depth of liquid on each tray and $d$ is the average density of the liquid on each tray.

The effective average temperature of the distillation zone may vary widely, depending on the pressure employed in the column, the overhead composition desired and other factors, but is generally from about 60° to about 80° C., and preferably about 65° to 75° C. The pressure in the distillation zone is not critical to the present invention, and one atmosphere of pressure has been found to be quite satisfactory although pressures above or below atmospheric may also be employed.

Overhead vapors produced in the distillation zone are withdrawn therefrom and passed to a condensing apparatus, (e.g. a reflux condenser) wherein the vapors are condensed. This condensate may be recycled as reflux to the distillation zone. Typically, the distillation is operated close to total reflux, that is with as much as 99 weight percent and more of distillate produced in the condensate is recycled as reflux to the distillation zone. The balance of the distillate may be withdrawn and discarded or sold as a source of chlorine and/or $C_1$ and $C_2$ hydrocarbons for preparation of industrial chlorinated solvents.

The distilled bottoms withdrawn from the distillation zone in which chorination is effected by the process of the present invention generally contains up to 99 weight percent ethylene dichloride and not greater than about 10 weight percent, and preferably not greater than about 5 weight percent, impurities (such as the trichlorobutenes formed by chlorination of chloroprenes) boiling at temperatures higher than the ethylene dichloride. This withdrawn bottoms may be passed to a second distillation zone for separation of ethylene dichloride from the higher boiling impurities by conventional distillation, and the substantially pure ethylene dichloride thereby obtained may be passed to a cracking furnace for production of vinyl chloride.

The process of the present invention may be further illustrated by reference to the following examples:

EXAMPLES 1-4

To a 1,000 ml. round-bottom glass flask equipped with a reflux condenser, thermometer and magnetic stirrer, is introduced a desired quantity of an ethylene dichloride stream comprising 63 weight percent ethylene dichloride, 25.2 weight percent chloroprene and 11.4 weight percent alpha-chloroprene (i.e. 36.6 weight percent total chloroprenes). The flask containing the ethylene dichoride mixture is maintained at the desired temperature by immersion of the reaction flask in a heated water bath. Chlorine gas is sparged to the flask, and the flask operated with continuous stirring under conditions of total reflux. The non-condensables are passed through a suck-back trap and then through two successive caustic scrubbers. The first scrubber contains 125 ml. of an 0.1 aqueous NaOH solution together with 125 ml. water, and the second scrubber contains 125 ml. of an 1.0N aqueous NaOH solution together with 125 ml. water. Light is excluded from the reaction vessel. By analysis of periodic samples drawn from the liquid present in the reaction vessel, it is determined that substantially all of the chloroprenes have been chlorinated at the times indicated in Table I below:

Table I

| Ex. | Grams EDC Mixture | Reaction Temp. | Chlorine Feed Rate (grams/min.) | Reaction Time (min.) | Weight Ratio Gms. $Cl_2$/Gm. Chloroprenes |
|---|---|---|---|---|---|
| 1 | 248 | 60-65° C | 0.42 | 165 | 0.76 |
| 2 | 248.5 | 61-65° C | 0.63 | 120 | 0.83 |
| 3 | 249 | 61-65° C | 0.82 | 90 | 0.81 |
| 4 | 252 | 69-70° C | 1.25 | 42 | 0.57 |

EXAMPLES 5-6

The procedure of Example 1 is repeated employing an ethylene dichoride stream comprising 89 weight percent ethylene dichloride, 4.0 weight percent alpha-chloroprene, and 6.6 weight percent chloroprene, i.e. 10.6 weight percent total chloroprenes, yielding the data set forth in Table II below:

Table II

| Ex. | Grams EDC Mixture | Reaction Temp. | Chlorine Feed Rate (grams/min.) | Reaction Time (min.) | Weight Ratio Gms. $Cl_2$/Gm. Chloroprenes |
|---|---|---|---|---|---|
| 5 | 253 | 61-66° C | 0.21 | 90 | 0.70 |
| 6 | 250 | 59-66° C | 0.42 | 60 | 0.95 |

The rate of chlorination of the chloroprenes present in the distillation zone may be accelerated by providing therein a source of radiation in the visible and/or ultraviolet spectrum. The effective spectrum extends from about 4785A in the visible region to about 2500A in the high ultraviolet. Thus, these chlorinations may be carried out with incandescent or fluorescent lighting. However, such radiation is not required in that the present invention has been found to effect chlorination of the chloroprenes in the substantial absence of light.

Although certain preferred embodiments of the invention have been disclosed for the purpose of illustration, it will be evident to one skilled in the art that various changes and modifications may be made therein without departing from the scope and spirit of the invention.

We claim:

1. In a process for recovering ethylene dichloride from an impure ethylene dichloride stream containing (i) impurities boiling at a temperature lower than the boiling point of ethylene dichloride and consisting at least in part of a chloroprene-impurity selected from the group consisting of chloroprene, alpha-chloroprene and mixtures thereof, and (ii) impurities boiling at a temperature higher than the boiling point of ethylene dichloride, wherein a. said impure ethylene dichloride stream is passed to a first distillation zone and distilled therein under conditions sufficient to provide (1) first distillate containing said lower boiling impurities and (2) first bottoms containing ethylene dichloride together with said higher boiling impurities, and b. said first bottoms is passed to a second distillation zone and distilled therein under conditions sufficient to provide (1) second distillate containing ethylene dichloride and (2) second bottoms containing said higher boiling impurities, the improvement which comprises chlorinating at least the portion of said chloroprene-impurity by introducing into said first distillation zone, during the distillation of ethylene dichloride therein, a gas containing elemental chlorine, thereby producing chloroprene reaction products having a boiling point higher than the boiling point of ethylene dichloride, and withdrawing said chloroprene reaction products with said first bottoms for passage to a second distillation zone.

2. The process according to claim 1 wherein said impure ethylene dichloride stream contains from about 80 to 98 weight percent ethylene dichloride and from about 0.05 to 6 weight percent chloroprenes.

3. The process according to claim 1 wherein said impure ethylene dichloride stream is distilled in said first distillation zone at a temperature of from about 60 to 80° C.

4. The process according to claim 1 wherein said gas containing elemental chlorine is introduced into said first distillation zone at a point in said zone to provide a quantity of liquid above said point sufficient to allow substantially complete chlorination of said chloroprenes.

5. The process according to claim 4 wherein the distillation in said first distillation zone is effected at a temperature of from about 60° to 70° C. and wherein the amount of liquid in said first distillation zone above the point at which the gas containing elemental chlorine is introduced is at least that amount of liquid, defined as $H_{min}$, determined according to the expression:

$$H_{min} = (C_{max}/0.523)$$

wherein $C_{max}$ is the maximum mass flow rate of said chloroprene-impurity introduced into said first distillation zone with said impure ethylene dichloride stream.

6. The process according to claim 1 wherein at least a portion of said first distillate is recycled to said first distillation zone.

* * * * *